(12) United States Patent
Prieto et al.

(10) Patent No.: US 8,592,590 B2
(45) Date of Patent: Nov. 26, 2013

(54) TETRAHYDROTRIAZOLOPYRIDINE COMPOUNDS AS SELECTIVE MGLU5 RECEPTOR POTENTIATORS USEFUL FOR THE TREATMENT OF SCHIZOPHRENIA

(75) Inventors: Lourdes Prieto, Madrid (ES); Lorena Taboada Martinez, Barcelona (ES)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/515,407

(22) PCT Filed: Dec. 21, 2010

(86) PCT No.: PCT/US2010/061406
§ 371 (c)(1),
(2), (4) Date: Jun. 12, 2012

(87) PCT Pub. No.: WO2011/082010
PCT Pub. Date: Jul. 7, 2011

(65) Prior Publication Data
US 2012/0252838 A1 Oct. 4, 2012

Related U.S. Application Data

(60) Provisional application No. 61/307,935, filed on Feb. 25, 2010.

(30) Foreign Application Priority Data

Dec. 29, 2009 (EP) ..................................... 09382309

(51) Int. Cl.
*C07D 513/02* (2006.01)
*A01N 43/42* (2006.01)

(52) U.S. Cl.
USPC .......................................... 546/119; 514/303

(58) Field of Classification Search
USPC .......................................... 546/119; 514/303
See application file for complete search history.

(56) References Cited

U.S. PATENT DOCUMENTS 7,456,200 B2 11/2008 Arora et al.
7,476,684 B2 1/2009 Minidis et al.
7,585,881 B2 9/2009 Edwards et al.

FOREIGN PATENT DOCUMENTS

| WO | 2004/014881 A3 | 2/2004 |
| WO | 2004/021984 A2 | 3/2004 |
| WO | 2005/080397 A2 | 9/2005 |
| WO | 2006/014185 A2 | 2/2006 |
| WO | 2006/018735 A2 | 2/2006 |
| WO | 2007/039781 A2 | 4/2007 |
| WO | 2007/130824 A2 | 11/2007 |
| WO | 2007/130825 A2 | 11/2007 |
| WO | 2009/045753 A1 | 4/2009 |

OTHER PUBLICATIONS

Ahn et al Progress in Neuro-Psychopharmacology & Biological Psychiatry 27 (2003) 993-999.*
Timofeeva et al Neuroscience 195 (2011) 21-36.*
Gilmour et al. Neuropharmacology, 2013, 64(1):224-39.*
Jonathan D. Sokolowski et al., The behavioral effects of sertraline, fluoxetine, and paroxetine differ on the differential-reinforcement-of-low-rate 72-second operant schedule in the rat, Psychopharmacology 1999, pp. 153-161, vol. 147.

* cited by examiner

*Primary Examiner* — Nizal Chandrakumar
(74) *Attorney, Agent, or Firm* — Mark A Winter

(57) ABSTRACT

The present invention provides certain tetrahydrotriazolopyridine derivatives, pharmaceutical compositions thereof, methods of using the same and processes for preparing the same. Formula (I) wherein $R^1$ is hydrogen, fluoro, chloro, or methyl; and $R^2$ is C4-C8 branched alkyl.

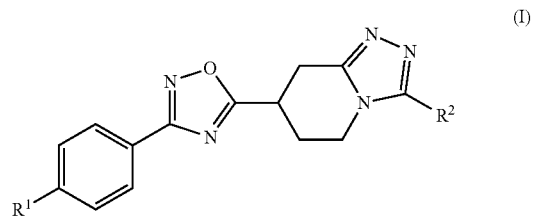

(I)

7 Claims, No Drawings

TETRAHYDROTRIAZOLOPYRIDINE COMPOUNDS AS SELECTIVE MGLU5 RECEPTOR POTENTIATORS USEFUL FOR THE TREATMENT OF SCHIZOPHRENIA

This application is a United States national phase entry, pursuant to 35 U.S.C. 371, of PCT/US2010/061406 filed Dec. 21, 2010, which claims the benefit of European Patent application number 09382309.4, filed Dec. 29, 2009, and U.S. provisional patent application No. 61/307,935, filed Feb. 25, 2010.

The present invention provides certain tetrahydrotriazolopyridine compounds, pharmaceutical compositions thereof, methods of using the same, and processes for preparing the same.

L-Glutamate is the major excitatory neurotransmitter in the central nervous system and is referred to as an excitatory amino acid. Glutamate receptors are composed of two major subtypes: the ligand-gated ion-channel ionotropic receptors, and the G-protein-coupled seven-transmembrane-domain metabotropic receptors (mGlu). The metabotropic family comprises eight members and is sub-divided into three groups based on sequence similarity, signal transduction, and pharmacology. Group I receptors (mGlu$_1$ and mGlu$_5$, and their splice variants) are positively coupled to inositol phosphate hydrolysis and the generation of an intracellular calcium signal. Group II receptors (mGlu$_2$ and mGlu$_3$) and Group III receptors (mGlu$_4$, mGlu$_6$, mGlu$_7$, and mGlu$_8$) are negatively coupled to adenylyl cyclase and regulate cyclic AMP levels by indirectly inhibiting adenylyl cyclase activity. The mGlu receptor subtypes have unique expression patterns in the central nervous system, which can be targeted with new and selective agents.

International Patent Application Publication Nos. WO 2007/130824 and WO 2007/130825 disclose certain triazolopyrimidine compounds as antagonists of the mGlu$_5$ receptor, and further disclose the compounds as useful in the treatment of a number of conditions including schizophrenia.

International Patent Application Publication No. WO 2005/080397 discloses certain fused heterocyclic compounds as antagonists of the mGlu$_5$ receptor, and further discloses the compounds as useful in the treatment of a number of conditions including schizophrenia.

International Patent Application Publication No. WO 2006/014185 discloses certain heteropolycyclic compounds as antagonists of Group I mGlu receptors, and further discloses the compounds as useful in the treatment of a number of conditions including schizophrenia.

The compounds of the present invention are selective potentiators of the Group I metabotropic receptors, particularly the mGlu$_5$ receptor (mGlu$_5$). In particular the compounds of the present invention demonstrate selectivity for the mGlu$_5$ receptor relative to mGlu$_1$ receptor. As such they are believed to be useful for the treatment of conditions associated with the mGlu$_5$ receptor such as schizophrenia including cognitive impairment associated with schizophrenia.

Thus, the present invention provides new compounds that are potentiators of mGlu$_5$ and, as such, are believed to be useful in treatment of the disorders discussed above. Such compounds should be useful in treating these conditions with an adverse event profile that differs from non-selective agents.

The present invention provides a compound of formula I, or a pharmaceutically acceptable salt thereof,

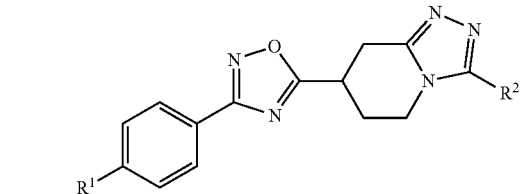

wherein
$R^1$ is hydrogen, fluoro, chloro or methyl; and
$R^2$ is C4-C5 branched alkyl.

Further, the present invention provides a pharmaceutical composition comprising a compound of the present invention, or a pharmaceutically acceptable salt thereof, and a pharmaceutically acceptable carrier, diluent or excipient.

In a particular embodiment, the composition further comprises one or more other therapeutic agents.

Further, the present invention provides a compound of the present invention or a pharmaceutically acceptable salt thereof, for use in therapy.

Further, the present invention provides a compound of the present invention, or a pharmaceutically acceptable salt thereof, for use in the treatment of schizophrenia.

Further, the present invention provides the use of a compound of the present invention, or a pharmaceutically acceptable salt thereof, for the manufacture of a medicament for treating schizophrenia.

Further, the present invention provides a method of treating schizophrenia, comprising administering to a patient in need thereof an effective amount of a compound of the present invention, or a pharmaceutically acceptable salt thereof.

A particular compound of formula I is one wherein $R^1$ is fluoro or a pharmaceutically acceptable salt thereof.

A particular compound of formula I is one wherein $R^2$ is tert-butyl or a pharmaceutically acceptable salt thereof.

A particular compound of formula I is one wherein
$R^1$ is hydrogen, fluoro, chloro or methyl; and
$R^2$ is tert-butyl, 1,1-dimethylpropyl, 2,2-dimethylpropyl, isobutyl, or 1,2-dimethylpropyl or a pharmaceutically acceptable salt thereof.

A particular compound of the present invention is 3-tert-butyl-7-[3-(4-fluorophenyl)-1,2,4-oxadiazol-5-yl]-5,6,7,8-tetrahydro[1,2,4]triazolo[4,3-a]pyridine or a pharmaceutically acceptable salt thereof.

A particular compound of the present invention is (−)-3-tert-butyl-(7S)-[3-(4-fluorophenyl)-1,2,4-oxadiazol-5-yl]-5,6,7,8-tetrahydro[1,2,4]triazolo[4,3-a]pyridine or a pharmaceutically acceptable salt thereof.

A particular compound of the present invention is (−)-3-tert-butyl-(7S)-[3-(4-fluorophenyl)-1,2,4-oxadiazol-5-yl]-5,6,7,8-tetrahydro[1,2,4]triazolo[4,3-a]pyridine, or a pharmaceutically acceptable salt thereof, substantially free of (+)-3-tert-butyl-(7R)-[3-(4-fluorophenyl)-1,2,4-oxadiazol-5-yl]-5,6,7,8-tetrahydro[1,2,4]triazolo[4,3-a]pyridine.

A further embodiment of the present invention includes a process for preparing a compound of formula I, or a pharmaceutically acceptable salt thereof, comprising A) for a compound of formula I,

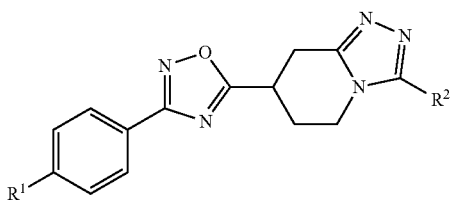

wherein
R¹ is hydrogen, fluoro, chloro or methyl; and
R² is C4-C5 branched alkyl;
condensing of a compound of formula VII with a compound of formula II wherein R³ is C1-C3 alkyl

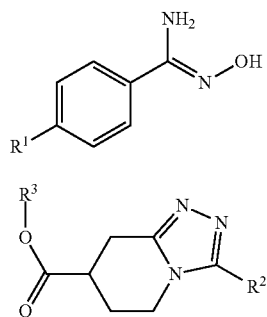

or alternatively
B) for a compound of formula I, condensing an R²-acyl hydrazine with a compound of formula III wherein X is O or S, and R⁴ is C1-C3 alkyl.

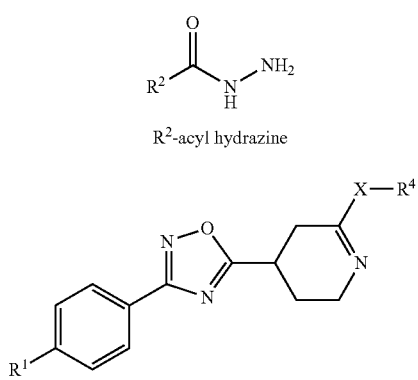

whereafter, when a pharmaceutically acceptable salt of the compound of formula I is desired, it is obtained by reacting a basic compound of formula I with a physiologically acceptable acid.

The term "C1-C3 alkyl" means a linear or branched alkyl chain having 1 to 3 carbon atoms.

The term "C4-C5 branched alkyl" means an alkyl chain having 4 to 5 carbon atoms wherein at least one carbon atom is tertiary or quaternary.

It is understood that compounds of the present invention may exist as stereoisomers. While all enantiomers, diastereomers, and mixtures thereof, are contemplated within the present invention, preferred embodiments are single diastereomers, and more preferred embodiments are single enantiomers. Even more preferred embodiments are single enantiomers substantially free of the other enantiomer. The term "substantially free" means an enantiomeric excess (ee) greater than 95%. An enantiomeric excess greater than 97% is preferred with an excess greater than 99% being more preferred.

The term "pharmaceutically acceptable salt" includes an acid addition salt that exists in conjunction with the basic portion of a compound of formula I. Such salts include the pharmaceutically acceptable salts listed in HANDBOOK OF PHARMACEUTICAL SALTS: PROPERTIES, SELECTION AND USE, P. H. Stahl and C. G. Wermuth (Eds.), Wiley-VCH, New York, 2002 which are known to the skilled artisan.

In addition to pharmaceutically acceptable salts, other salts are included in the invention. They may serve as intermediates in the purification of compounds or in the preparation of other pharmaceutically-acceptable salts, or are useful for identification, characterization or purification.

A compound of the invention is expected to be useful whenever potentiation of the mGluR₅ receptor is indicated. In particular, a compound of the invention is expected to be useful for the treatment of schizophrenia including cognitive impairment associated with schizophrenia.

As used herein, the term "patient" refers to a warm blooded animal such as a mammal and preferably refers to a human.

It is recognized that one skilled in the art may affect schizophrenia by treating a patient presently displaying symptoms with an effective amount of the compound of the present invention. Thus, the terms "treatment" and "treating" are intended to refer to all processes wherein there may be a slowing, interrupting, arresting, controlling, or stopping of the progression of the disorder and/or symptoms thereof, but does not necessarily indicate a total elimination of all symptoms.

As used herein, the term "effective amount" of a compound of formula I refers to an amount, that is, the dosage which is effective in treating schizophrenia as described herein.

The attending diagnostician can readily determine an effective amount by the use of conventional techniques and by observing results obtained under analogous circumstances. In determining an effective amount, the dose of a compound of the present invention, a number of factors are considered by the attending diagnostician, including, but not limited to the compound of the present invention to be administered; the co-administration of other agents, if used; the species of mammal; its size, age, and general health; the degree of involvement or the severity of the symptoms; the response of the individual patient; the mode of administration; the bioavailability characteristics of the preparation administered; the dose regimen selected; the use of other concomitant medication; and other relevant circumstances.

An effective amount of a compound of the present invention is expected to vary from about 0.01 milligram per kilogram of body weight per day (mg/kg/day) to about 5 mg/kg/day. Preferred amounts may be determined by one skilled in the art.

The compounds of the present invention can be administered alone or in the form of a pharmaceutical composition, that is, combined with pharmaceutically acceptable carriers or excipients, the proportion and nature of which are determined by the solubility and chemical properties, including stability, of the compound selected, the chosen route of administration, and standard pharmaceutical practice. The compounds of the present invention, while effective themselves, may be formulated and administered in the form of their pharmaceutically acceptable salts, for convenience of crystallization, increased solubility, and the like.

One skilled in the art of preparing formulations can readily select the proper form and mode of administration depending upon the particular characteristics of the compound selected, the disorder or condition to be treated, the stage of the disorder or condition, and other relevant circumstances (REMINGTON: THE SCIENCE AND PRACTICE OF PHARMACY, 19th Edition, Mack Publishing Co. (1995)).

Functional in vitro Activity at Human mGlu$_5$ Receptor

An AV-12 cell line stably expressing the human mGlu$_5$ receptor and co-transfected with the rat glutamate transporter EAAT 1 (Excitatory Amino Acid Transporter 1) are used for these studies (see for example Desai, Burnett, Mayne, Schoepp, *Mol. Pharmacol.* 48, 648-657, 1995). The cell line is maintained by culturing in Dulbecco's Modified Eagle's Medium (DMEM) with high glucose and pyridoxine hydrochloride supplemented with 5% heat inactivated, dialyzed fetal bovine serum, 1 mM sodium pyruvate, 10 mM HEPES (4-(2-hydroxyethyl)-1-piperazineethanesulfonic acid), 1 mM of L-glutamine, 0.75 mg/ml geneticin and 0.3 mg/ml hygromycin. Sub-confluent cultures are passaged twice per week using 0.25% trypsin-EDTA. Cells are harvested 24 hours prior to assay and dispensed using a Matrix Well-Mate cell seeder at 65,000 cells per well into 96-well, black-walled, poly-D-lysine-coated plates in medium containing 1 mM L-glutamine (freshly added).

Intracellular calcium levels are monitored before and after the addition of compounds using a Fluorometric Imaging Plate Reader (FLIPR, Molecular Devices, Union City, Calif. USA). The assay buffer is comprised of Hank's Buffered Salt Solution (HBSS) supplemented with 20 mM HEPES. The medium is removed and the cells are incubated with 8 µM Fluo-3 AM (Molecular Probes, Eugene, Oreg., USA, F-1241; 50 µL per well) in assay buffer for 90 minutes at 25° C. The dye solution is removed and replaced with fresh assay buffer (50 µL per well). A single-addition FLIPR assay generating an 11-point concentration response curve for the agonist glutamate is conducted prior to each experiment. The results are analyzed using (GraphPad® Prism v4, Graphpad Software, LaJolla, Calif., USA) to calculate the concentrations of glutamate needed to induce the EC$_{10}$ responses.

Compounds are tested in a two-addition FLIPR assay using a 10-point concentration response profile starting at a final concentration of 25 µM (agonist mode) or 12.5 µM (potentiator mode). A 3-fold dilution series in dimethyl sulfoxide (DMSO) is followed by a single dilution into assay buffer; the final concentration of DMSO is 0.625%. After taking an initial 5-sec fluorescent read on the FLIPR instrument, compound is added to the cell plate (50 ul per well). Data are collected every second for the first 30 seconds and then every 3 seconds for a total of 90 seconds in order to detect agonist activity Immediately thereafter, the second addition consisting of 100 µl of glutamate in assay buffer (typically about 1-2 µM, final) is added to the cell plate, generating an EC$_{10}$ response. Following the second addition, data are collected every second for 29 images and then every 3 seconds for 15 images.

The maximal response is defined as that induced by ECmax (100 µM glutamate). The compound effect is measured as maximal minus minimal peak heights in relative fluorescent units (RFUs) corrected for basal fluorescence measured in the absence of glutamate. Determinations are carried out using duplicate plates. Agonist effects are quantified as percent stimulation induced by compound alone relative to the maximal glutamate response. Potentiation effects are quantified as percent increase in the presence of an EC$_{10}$ response in glutamate relative to the EC$_{max}$ response. All data are calculated as relative EC$_{50}$ values using a four parameter logistic curve fitting program (ActivityBase® v5.3.1.22, IBS, Alamenda, Calif., USA).

In the above assay, compounds exemplified in racemic form herein exhibited an EC$_{50}$ in potentiator mode of less than 12 µM at mGlu$_5$. For example, the compound of Example 1 exhibited an EC$_{50}$ of 120±47 nM (n=3) measured at mGlu$_5$. Further, compounds exemplified in resolved form herein exhibited an EC$_{50}$ in potentiator mode less than 200 nM at mGlu$_5$. For example, the compound of Example 11 exhibited an EC$_{50}$ of 36±3.5 nM (n=6) measured at mGlu$_5$. This demonstrates that compounds of the present invention are potentiators of the human mGlu$_5$ receptor.

Delayed Matching to Position Task in Rats

The delayed matching to position task (DMTP) has been used to study working memory in rats. Working memory in this context is the retention and use of information that is available only during an individual trial. The study of compounds which modulate NMDA receptors in DMTP has been used to identify the importance of NMDA receptors in learning and memory. More specifically, studies have shown competitive NMDA antagonists to induce impairment of DMTP in rats. Compounds which show a positive effect in attenuating deficits induced by competitive NMDA antagonists in rats are believed to be useful in treating cognitive disorders in humans.

Male Lister hooded rats are housed in groups of 4 and are maintained on a food-restricted diet and a 12-hour light dark cycle. The experiments are conducted during the same part of the light phase each day.

Standard operant chambers, housed in sound and light attenuating chambers are used. Each chamber comprised a house light, two retractable levers, each with a stimulus light above it. The levers are located either side of a recessed magazine where food pellets are delivered from an automatic pellet dispenser. Start of a session is signaled by onset of the house light, and its permanent offset indicated the end of a session. Experimental sessions are controlled and data is recorded and analyzed.

Sample Phase. A trial begins with a one of the levers extending into the chamber. The stimulus light above the lever is illuminated. If the lever is pressed, it is retracted and the stimulus light extinguished. This initiates the pseudo-randomly selected delay period of 1, 2, 4, 8 or 16 seconds during training or 1, 12, or 32 seconds during test.

Head Entry. After this delay period is complete, animals are required to make a head entry into the food hopper within 10 seconds, if an appropriate response is made both levers are extended into the chamber. If no response is made during this period, the house-light is extinguished and the trial counted as an omission.

Choice Phase. If animals make the appropriate head entry response and the levers extended into the operant chamber, they have 10 seconds which to make their response. A correct response consists of an animal pressing the same lever that is extended into the chamber during the sample phase. This response results in both levers retracting and a single food pellet being delivered into the food hopper. After a 5 second inter-trial interval the next trial begins. Following an incorrect response, (the animal pressing the opposite lever as had been extended during the sample phase), both levers retract and the house-light is extinguished signaling the end of that trial. After a 5 second time out the next trial begins, signaled by onset of the house-light. If the animal fails to respond within 10 second during the choice phase, the levers retract, the house-light extinguishes and the trial is recorded as an omission.

Overall Session. Each session is terminated after 75 trials (15 pseudo-random presentations of each delay period). Animals are trained to a criterion of greater than 70% accuracy over the entire session with less than 10% omissions of responding. After criterion is reached, rats are trained two times a week in a baseline condition and once a week in a test condition.

Test Compounds. A compound of the present invention stock of 1.0 mg/ml is prepared. For example, 18.7 mg of the compound of Example 11 is weighed and suspended in 18.7 ml vehicle (1% high viscocity cmc, 0.25% tween, 0.05% antifoam). A white suspension is formed. Test compound is administered orally, 60 minutes prior to the start of a session, in a volume of 1 ml/kg.

NMDA antagonist stock, 2.0 mg/ml: 35.5 mg of SDZ 220,581 is weighed and dissolved in 16.73 ml vehicle (0.09 ml 1M NaOH, made up to volume with 5% glucose). A solution is formed and at a pH 6.5 at time of injection. SDZ 220,581 is administered subcutaneously, 30 minutes prior to the start of a session, in a volume of 1 ml/kg. The NMDA antagonist SDZ 220,581 or SDZ refers to (S)-α-amino-2'-chloro-5-(phosphonomethyl)[1,1'-biphenyl]-3-propanoic acid.

Statistical Analysis. Animals are assigned to treatment groups counterbalanced for previous treatments and baseline performance. A 2-way factorial ANOVA factors: Example 11_ (E.11 or V) and SDZ 220,581_ (SDZ or V) is conducted on single measures including head entries, trials etc. A three-way ANOVA is conducted on repeated measures (2 between—E.11, SDZ) and one within factor (delay). Significant main effects and interactions are followed up with appropriate planned comparisons. If significant effects of treatment are present but no significant interaction, the interaction is further assessed with planned comparisons and analysis of simple effects.

Results (see Table 1). Analysis of counterbalancing of treatment groups matched showed that the groups did not differ prior to test. There is no significant effect of assigned treatment on any of the key measures—total % correct $F_{3,60}=0.005$; total % incorrect $F_{3,60}=0.001$; total % omissions $F_{3,60}=0.11$. There is no difference between groups on the number of head entries made during the session ($F_{3,60}=1.38$). Nor is there any effect of assigned treatment on % correct at each delay (treatment×delay $F_{12,240}=1.09$). 64 animals are included in the study.

% Accuracy: There is a main effect of Example 11 treatment ($F_{1,60}=6.4$, $P<0.05$); and a main effect of SDZ_treatment ($F_{1,60}=8.0$, $P<0.01$). The interaction is significant ($F_{1,60}=5.6$, $P<0.05$). Planned comparisons show V/SDZ performs significantly worse than V/V treated animals and that this deficit is completely abolished by concomitant treatment with Example 11.

% Omissions: There is a main effect of Example 11 treatment ($F_{1,60}=6.75$, $P<0.05$); and a main effect of SDZ_treatment ($F_{1,60}=15.66$, $P<0.001$). The interaction is significant ($F_{1,60}=9.61$, $P<0.01$). Planned comparisons show V/SDZ performs significantly worse than V/V treated animals and that this deficit is completely abolished by concomitant treatment with Example 11.

Latency Measures: There is no main effect on average latency to respond correctly of Example 11 treatment ($F_{1,60}=2.98$); nor a main effect of SDZ_treatment ($F_{1,60}=11.26$, $P<0.01$). The interaction is a significant ($F_{1,60}=5.48$, $P<0.05$). Planned comparisons show V/SDZ performs significantly worse than V/V treated animals and that this deficit is attenuated by concomitant treatment with Example 11. There is no main effect on average latency to respond incorrectly of Example 11 treatment ($F_{1,60}=2.37$, $P>0.1$); nor a main effect of SDZ_treatment ($F_{1,60}=12.20$, $P<0.001$). The interaction is not significant ($F_{1,60}=3.81$, $P>0.05$). Planned comparisons show that V/SDZ performs significantly worse than V/V treated animals and that this deficit is attenuated by concomitant treatment with Example 11. There is no main effect on the latency to press the sample lever during the 75 trial session of Example 11 treatment ($F_{1,60}=1.65$); nor a main effect of SDZ_treatment ($F_{1,60}=18.55$, $P<0.001$). The interaction is not significant ($F_{1,60}=2.76$). Planned comparisons show that V/SDZ performs significantly worse than V/V treated animals and that this deficit is attenuated by concomitant treatment with Example 11.

Head Entries: There is a main effect on total head entries of Example 11 treatment ($F_{1,60}=9.02$, $P<0.01$); and a main effect of SDZ_treatment ($F_{1,60}=11.20$, $P<0.01$). The interaction is significant ($F_{1,60}=8.31$, $P<0.01$). Planned comparisons show that V/SDZ performs significantly worse than V/V treated animals and that this deficit is attenuated by concomitant treatment with Example 11.

Trials Completed: There is no main effect on the number of trials completed of Example 11_treatment ($F_{1,60}=0.27$), nor a main effect of SDZ_treatment ($F_{1,60}=5.95$, $P<0.05$). The interaction is not significant ($F_{1,60}=0.27$). Planned comparisons show that V/V is significantly different to V/SDZ.

TABLE 1

| Measure | V/V | Example 11/V | Example 11/SDZ | V/SDZ |
|---|---|---|---|---|
| % Accuracy | 75.3 ± 1.4 | 75.6 ± 1.6 | 74.7 ± 2.0+++ | 66.0 ± 2.0*** |
| % Omissions | 0.5 ± 0.2 | 1.2 ± 0.4 | 2.3 ± 1.0+++ | 9.9 ± 2.4*** |
| Head Entries | 2080 ± 125 | 2092 ± 83 | 2043 ± 115+++ | 1421 ± 95 |
| Trials Completed | 75 ± 0 | 75 ± 0 | 72 ± 2 | 71 ± 2* |
| Average Correct latency (s) | 0.91 ± 0.05 | 0.94 ± 0.05 | 0.99 ± 0.06++ | 1.21 ± 0.05*** |
| Average Incorrect latency (s) | 0.95 ± 0.07 | 0.98 ± 0.08 | 1.10 ± 0.07+ | 1.35 ± 0.07*** |
| Sample latency (s) | 1.32 ± 0.09 | 1.84 ± 0.22 | 5.77 ± 2.09+ | 10.1 ± 2.06*** |
| N | 16 | 16 | 16 | 16 |

Compared with V/V: *$0.01 < p < 0.05$; $0.001 < p < 0.01$; *$p < 0.001$
Compared with V/SDZ: +$0.01 < p < 0.05$; ++$0.001 < p < 0.01$; +++$p < 0.001$ In the above assay, concurrent treatment with 1 mg/kg Example 11 attenuated all deficits induced by SDZ-220,581 in the delayed matching to position assay of working memory. This demonstrates that a compound of the present invention is useful in an in vivo model of cognition.

A compound of formula I may be prepared by a process known to one of ordinary skill in the chemical art for the production of structurally analogous compounds or by a process described herein including those described for the Preparations and Examples. A novel process described herein provides another aspect of the invention. A process for the preparation of a compound of formula I, or a pharmaceutically acceptable salt thereof, and novel intermediates for the manufacture of a compound of formula I provide further features of the invention and are illustrated by the following procedures in which the meaning of the generic radicals are as defined above, unless otherwise specified.

Scheme A

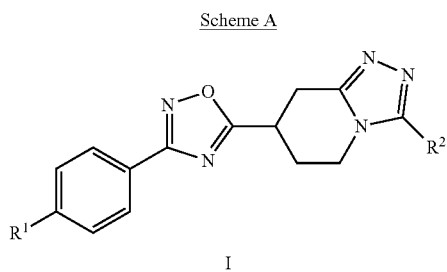

I

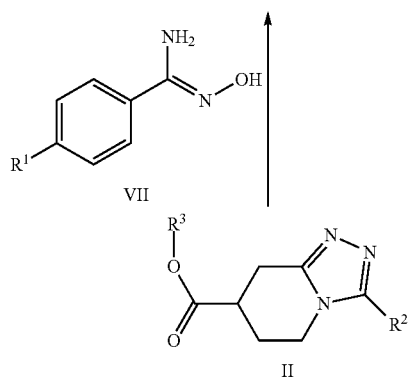

VII

II

Generally, a compound of formula I may be prepared from a compound of formula II. More specifically in Scheme A, a compound of formula II where $R^3$ is C1-C3 alkyl is condensed with an $R^1$-benzamidoxime of formula VII in the presence of a base such as potassium tert-butoxide in a suitable solvent, such as tetrahydrofuran to provide a compound of formula I.

Scheme B

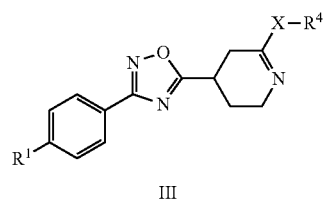

I

III

A compound of formula I may also be prepared from a compound of formula III. More specifically in Scheme B, a compound of formula III where X is O or S, and $R^4$ is C1-C3 alkyl is reacted with an $R^2$-acyl hydrazine in a suitable solvent, such as methanol to provide a compound of formula I.

Scheme C

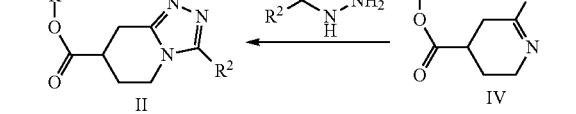

II IV

A compound of formula II may be prepared from a compound of formula IV. More specifically in Scheme C, a compound of formula IV where where X is O or S, and $R^4$ is C1-C3 alkyl is reacted with an $R^2$-acyl hydrazine in a suitable solvent such as methanol or pyridine to provide a compound of formula II.

Scheme D

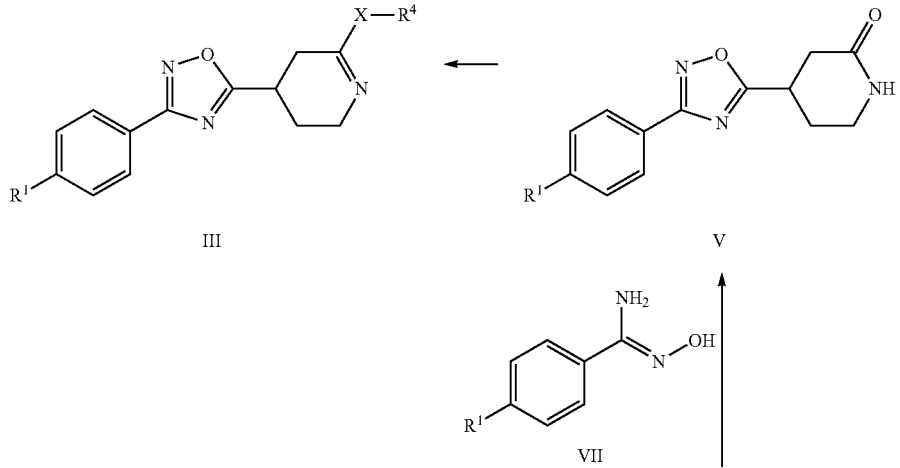

III V

VII

-continued

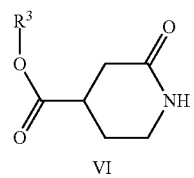

VI

A compound of formula III may be prepared from a compound of formula VI. More specifically in Scheme D, a compound of formula VI where $R^3$ is C1-C3 alkyl is condensed with an $R^1$-benzamidoxime of formula VII in the presence of a base, such as potassium tert-butoxide in a suitable solvent, such as tetrahydrofuran to provide a compound of formula V. A compound of formula V is reacted with an alkylating agent such as trimethyloxonium tetrafluoroborate in a suitable solvent, such as dichloromethane to provide a compound of formula III where X is oxygen and $R^4$ is methyl.

In the following illustrative preparations and examples, the following meanings and abbreviations are used throughout: DMSO, dimethyl sulfoxide (perdeuterated [-$d_6$] if for NMR); MS, mass spectrum; EtOAc, ethyl acetate; THF, tetrahydrofuran; min, minutes; HPLC, high pressure liquid chromatography; LC-MS, HPLC-mass spectrography; GC, gas chromatography; MeOH, methanol; MTBE, methyl t-butyl ether; SCX-2, cation exchange resin; mp, melting point; and NMR, nuclear magnetic resonance spectroscopy or spectrum. As used herein, "δ" refers to part per million down-field from tetramethylsilane. The term k' refers to capacity factor. Reagents are obtained from a variety of commercial sources. Solvents are generally removed under reduced pressure (evaporated). In some preparations indicated yields are representative crude yields for products which are isolated by evaporation or filtration and used directly without further purification. Racemic compounds maybe designated with or without the (±) symbol in the chemical name.

Preparation 1

Synthesis of methyl piperidine-2-thione-4-carboxylate

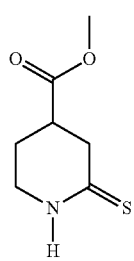

Add Lawesson's reagent (9.2 g, 22.7 mmol) to a solution of methyl 2-oxopiperidine-4-carboxylate (6.5 g, 41.4 mmol) in toluene (83 mL) and heat to reflux for 2 hours. Cool the solution and concentrate to dryness under reduced pressure. Purify the residue by flash chromatography on silica gel, eluting with ethyl acetate:dichloromethane (gradient 5-15%) to afford the title compound (6.95 g). $^1$H NMR (CDCl$_3$) δ 1.97 (m, 1H), 2.17 (m, 1H), 2.78 (m, 1H), 3.03 (m, 1H), 3.24 (m, 1H), 3.39 (m, 1H), 3.49 (m, 1H), 3.72 (s, 3H), 8.48 (bs, 1H).

Preparation 2

Synthesis of methyl 2-methylthio-3,4,5,6-tetrahydropyridine-4-carboxylate trifluoromethanesulfonic acid

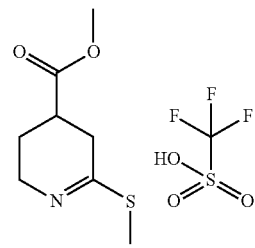

Add methyl trifluoromethanesulfanate (7.9 g, 48.1 mmol) to a solution of methyl piperidine-2-thione-4-carboxylate (6.95 g, 40.1 mmol) in dichloromethane (150 mL). After 16 hours, concentrate under reduced pressure to afford the title compound (13.68 g). $^1$H NMR (CDCl$_3$) δ 2.09 (m, 1H), 2.35 (m, 1H), 2.74 (s, 3H), 3.05 (m, 3H), 3.74 (s, 3H), 3.87 (m, 2H).

Preparation 3

Synthesis of methyl 3-tert-butyl-5,6,7,8-tetrahydro-[1,2,4]triazolo[4,3-a]pyridine-7-carboxylate

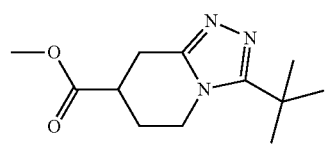 [SMILES: COC(=O)C1CCn2c(nnc2C(C)(C)C)C1]

Add pivaloyl hydrazide (4.95 g, 42.6 mmol) to a solution of methyl 2-methylthio-3,4,5,6-tetrahydropyridine-4-carboxylate trifluoromethanesulfonic acid (13.68 g, 40.55 mmol) in pyridine (25 mL) and stir for 16 hours. Heat to 60° C. for 2 hours and concentrate under reduced pressure after cooling. Dissolve in dichloromethane and add a 1:1 mixture of saturated aqueous sodium bicarbonate and 10% aqueous potassium carbonate. Separate the organic layer and extract the aqueous with additional dichloromethane. Combine the organics, wash with brine, and dry over anhydrous sodium sulfate. Filter and concentrate the filtrate under reduced pressure to afford the title compound (6.07 g, 56.8%). $^1$H NMR (CDCl₃) δ 1.44 (s, 9H), 2.11 (m, 1H), 2.34 (m, 1H), 2.85 (m, 1H), 3.1 (m, 1H), 3.33 (m, 1H), 3.76 (s, 3H), 3.96 (m, 1H), 4.28 (m, 1H).

Preparation 4

Synthesis of 1-tert-butyl 4-ethyl-2-oxopiperidine-1,4-dicarboxylate

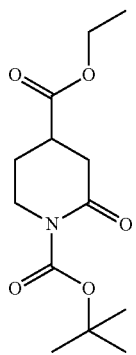 [SMILES: CCOC(=O)C1CCN(C(=O)OC(C)(C)C)C(=O)C1]

To a solution of 1-tert-butyl-4-ethyl-piperidine-1,4-dicarboxylate (75 g, 291.4 mmol) in acetonitrile (150 mL) and water (750 mL) at room temperature, add ruthenium (IV) oxide hydrate (2.2 g, 14.573 mmol) (99.9%) to give a fine black suspension. Fit a water bath at 21° C. to aid cooling. Add sodium periodate (130 g, 606.2 mmol) portion-wise over 60 minutes keeping the temperature below 35° C. and only adding additional periodate when the internal temperature has cooled to below 30° C. After addition is complete, the reaction is stirred for 30 minutes at 25° C. Additional periodate (10 g) is added until the reaction remains yellow indicating completion.

Pour the mixture into water (2000 mL) and dichloromethane (1000 mL). Filter through diatomaceous earth and wash the filter cake with dichloromethane. Separate filtrate layers and extract the aqueous phase with further dichloromethane. Combine the organics, dry over anhydrous magnesium sulfate, filter, and concentrate to dryness under reduced pressure. Purify the resulting residue on a plug of silica gel, eluting with 100% hexane and then 40% ethyl acetate/hexane. Concentrate the appropriate fractions containing the product to give the title compound as a pale yellow oil (69.5 g). ¹H NMR (DMSO-d₆) δ 1.16 (t, 3H), 1.4 (s, 9H), 1.82 (m, 1H), 2.05 (m, 1H), 2.95 (m, 1H), 2.45-2.55 (m, 2H), 3.47-3.6 (m, 2H), 4.07 (q, 2H).

Alternative preparation of 1-tert-butyl-4-ethyl 2-oxopiperidine-1,4-dicarboxylate Add ruthenium (IV) oxide hydrate (32 g, 0.21 mol) to a solution of 1-tert-butyl-4-ethyl-piperidine-1,4-dicarboxylate (1100 g, 4.27 mol) in acetonitrile (11 L) and water (2.2 L) at room temperature. Add portion wise sodium periodate (1898.3 g, 8.85 mol) and stir the reaction mixture at room temperature for 2 hours. Filter the mixture through a pad of filter cell and dilute the filtrate with dichloromethane and water. Separate organic phase and dry over magnesium sulfate, filter, and concentrate to dryness under reduced pressure to obtain 1.15 Kg of the crude product. Purify the crude residue by filtering through a silica gel pad (hexane/EtOAc 20% to Hexane/EtOAc 50%) to provide the title compound as a pale yellow oil (1.04 Kg). Mass spectrum (m/z): 272 (M+1).

Preparation 5

Synthesis of 2-oxopiperidine-4-carboxylic acid ethyl ester

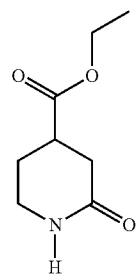

Add 4N hydrogen chloride in dioxane (26 mL, 103 mmol) to 1-tert-butyl-4-ethyl 2-oxopiperidine-1,4-dicarboxylate (20.0 g, 73.72 mmol) in dichloromethane (147 mL). Stir the reaction for 1 hour, concentrate under reduced pressure, and purify by flash chromatography eluting with 5% methanol in dichloromethane to afford the title compound (11.3 g). ¹H NMR (CDCl₃) δ 1.26 (t, 3H), 1.88 (m, 1H), 2.1 (m, 1H), 2.52-2.59 (m, 2H), 2.8 (m, 1H), 3.26-2.41 (m, 2H), 4.17 (q, 2H), 6.68 (bs, 1H).

Alternative preparation of 2-oxopiperidine-4-carboxylic acid ethyl ester

Add 4N HCl in dioxane (1.3 L) to a solution of 1-tert-butyl-4-ethyl 2-oxopiperidine-1,4-dicarboxylate (1 Kg, 3.69 mol) in dichloromethane (3.68 L). Stir the reaction overnight at room temperature. Cool to 0° C. and adjust to pH 8 with a solution of saturated aqueous sodium bicarbonate (7 L). Separate layers and extract the aqueous phase with additional dichloromethane (2×1 L). Combine the organic phases, dry over magnesium sulfate, filter, and concentrate to obtain the title compound (558.3 g). Mass spectrum (m/z): 172 (M+1).

Preparation 6

Synthesis of 2-methoxy-3,4,5,6-tetrahydro-pyridine-4-carboxylic acid ethyl ester

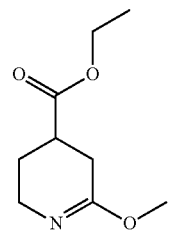

Add 2-oxopiperidine-4-carboxylic acid ethyl ester (6.0 g, 35 mmol) to a solution of trimethyloxonium tetrafluoroborate (9.0 g, 59.6 mmol) in dichloromethane (78 mL) cooled to 0° C. Stir the reaction for 3 hours and pour into an ice cold solution of saturated aqueous sodium bicarbonate. Separate layers and extract the aqueous layer with additional dichloromethane. Combine the organic layers, dry over anhydrous sodium sulfate, filter, and concentrate under reduced pressure to afford the title compound which was used without further purification (5.87 g, 90%). Mass spectrum (m/z): 186 (M+1).

Alternative preparation of 2-methoxy-3,4,5,6-tetrahydro-pyridine-4-carboxylic acid ethyl ester Add trimethyloxonium tetrafluoroborate (530.7 g) to a solution of 2-oxopiperidine-4-carboxylic acid ethyl ester (307.7 g, 1.80 mol) in dry dichloromethane (4.68 L) under nitrogen, and stir the reaction at room temperature for 16 hours. Cool the mixture to 0° C. and adjust to pH 8 with saturated aqueous sodium bicarbonate. Separate the layers and extract the aqueous phase with additional dichloromethane (2×1 L). Combine the organic phases, dry over magnesium sulfate, filter, and concentrate to provide the title compound (273.68 g). Mass spectrum (m/z): 186 (M+1).

Preparation 7

Synthesis of ethyl 3-tert-butyl-5,6,7,8-tetrahydro[1,2,4]triazolo[4,3-a]pyridine-7-carboxylate

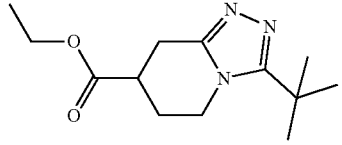 [SMILES: CCOC(=O)C1CCn2c(nnc2C(C)(C)C)C1]

Add pivaloyl hydrazide (3.68 g, 31.7 mmol) to a solution of 2-methoxy-3,4,5,6-tetrahydro-pyridine-4-carboxylic acid ethyl ester (5.87 g, 31.7 mmol) in methanol (16 mL) and heat to reflux overnight. Cool and concentrate under reduced pressure. Partition the resulting residue between dichloromethane and saturated aqueous sodium bicarbonate. Separate the layers and extract the aqueous layer with additional dichloromethane. Combine the organic phases, dry over anhydrous sodium sulfate, filter, and concentrate under reduced pressure to afford the title compound (7.05 g). $^1$H NMR (CDCl$_3$) δ 1.25 (t, 3H), 1.42 (s, 9H), 2.1 (m, 1H), 2.33 (m, 1H), 2.83 (m, 1H), 3.09 (m, 1H), 3.3 (m, 1H), 3.9 (m, 1H), 4.17 (q, 2H), 4.25 (m, 1H).

Alternative preparation of ethyl 3-tert-butyl-5,6,7,8-tetrahydro[1,2,4]triazolo[4,3-a]pyridine-7-carboxylate Add pivaloyl hydrazide (175 g) to a solution of 2-methoxy-3,4,5,6-tetrahydro-pyridine-4-carboxylic acid ethyl ester (273.68 g, 1.47 mol) in ethanol (2.2 L) under nitrogen at room temperature. Heat the mixture under reflux overnight for 16 hours. Cool to room temperature and concentrate to dryness under reduced pressure. To the resulting residue, add a solution of saturated sodium bicarbonate and extract with dichloromethane (3×1 L). Dry the combined organic phases over magnesium sulfate, filter, and concentrate to dryness under reduced pressure. Purify the resulting solid by trituration with methyl-tert-butyl ether to afford 293 g of the title compound. Mass spectrum (m/z): 252 (M+1).

The following compound is prepared essentially by the method of Preparation 7.

| Prep. No. | Chemical name | Structure | Physical data |
|---|---|---|---|
| 8 | ethyl 3-(1,1-dimethylpropyl)-5,6,7,8-tetrahydro-[1,2,4]triazolo[4,3-a]pyridine-7-carboxylate | 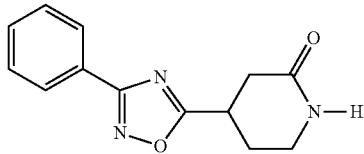 [SMILES: O=C1CC(c2nc(-c3ccccc3)no2)CCN1] | $^1$H NMR (CDCl$_3$) δ 0.77 (t, 2H), 1.26 (t, 3H), 1.42 (s, 6H), 1.75 (m, 2H), 2.12 (m, 1H), 2.33 (m, 1H), 2.85 (m, 1H), 3.1 (m, 1H), 3.34 (m, 1H), 3.9 (m, 1H), 4.14-4.29 (m, 3H). |

Preparation 9

Synthesis of 4-(3-phenyl-1,2,4-oxadiazol-5-yl)piperidin-2-one

Add benzamidoxime (5.63 g, 41.36 mmol) to a 1M solution of potassium t-butoxide (31 mL, 31 mmol) in tetrahydrofuran and anhydrous tetrahydrofuran (442 mL). Add methyl 2-oxopiperidine-4-carboxylate (5 g, 31.8 mmol) and stir overnight at room temperature. Pour reaction over saturated aqueous sodium bicarbonate and extract into chloroform. Separate layers and extract the aqueous phase with additional chloroform. Dry the combined organic layers over anhydrous magnesium sulfate, filter, and concentrate to dryness under reduced pressure. Purify the resulting residue by flash chromatography (silica gel), eluting with 1-5% 7 N ammoniated methanol in dichloromethane to afford the title compound (4.15 g). $^1$H NMR (CDCl$_3$) δ 2.19 (m, 1H), 2.34 (m, 1H), 2.8-2.95 (m, 2H), 3.44-3.52 (m, 2H), 3.57 (m, 1H), 6.13 (bs, 1H), 7.45-7.54 (m, 3H), 8.0-8.11 (m, 2H).

Preparation 10

Synthesis of 5-(2-methoxy-3,4,5,6-tetrahydropyridin-4-yl)-3-phenyl-1,2,4-oxadiazole

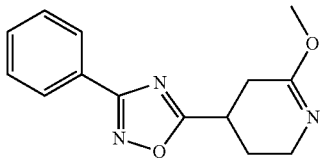 [SMILES: COC1=NCCC(c2nc(-c3ccccc3)no2)C1]

Add 4-(3-phenyl-1,2,4-oxadiazol-5-yl)piperidin-2-one (1.0 g, 4.11 mmol) to a solution of trimethyloxonium tetrafluoroborate (1.06 g, 6.99 mmol) in dichloromethane (8.2 mL) at 0° C. Stir the reaction overnight at room temperature and pour into an ice cold solution of saturated aqueous sodium bicarbonate. Separate and extract the aqueous layer with additional dichloromethane. Combine the organic layers, dry over anhydrous sodium sulfate, filter, and concentrate under reduced pressure to afford the title compound as a crystalline white solid (0.96 g). $^1$H NMR (CDCl$_3$) δ 1.9 (m, 1H), 2.17 (m, 1H), 2.65-2.72 (m, 2H), 3.43 (m, 1H), 3.58 (m, 1H), 3.7 (s, 3H), 3.75 (m, 1H), 7.43-7.53 (m, 3H), 8.0-8.1 (m, 2H).

Preparation 11

Synthesis of 2,2-dimethyl-butyric acid ethyl ester

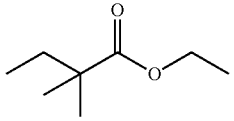

Add 0.2 mL of concentrated hydrochloric acid to 2,2-dimethyl-butanoic acid (5.0 g, 43.0 mmol) in ethanol (43 mL) and heat to reflux for 5 hours. Cool to room temperature. Pour the reaction into water and extract with diethyl ether. Wash the combined organics with saturated aqueous sodium bicarbonate and water, dry over magnesium sulfate, filter, and concentrate under reduced pressure to afford the title compound which was used without further purification (4.0 g, 64.4%): $^1$H NMR (CDCl$_3$) δ 0.82 (t, 3H, 1.14 (s, 3H), 1.23 (t, 3H), 1.55 (q, 2H), 4.1 (q, 2H).

The following compound is prepared essentially by the method of Preparation 11.

| Prep. No. | Chemical name | Structure | Physical data |
|---|---|---|---|
| 12 | ethyl 2,3-dimethylbutanoate | 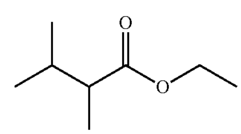 | $^1$H NMR (CDCl$_3$) δ 0.90 (t, 6H), 1.09 (d, 3H), 1.24 (t, 3H), 1.89 (m, 1H), 2.2 (m, 1H), 4.07-4.16 (m, 2H). |

Preparation 13

Synthesis of 2,2-dimethylbutanehydrazide

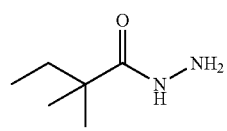

Reflux a mixture of hydrazine monohydrate (0.97 g, 19.4 mmol) and 2,2-dimethyl-butyric acid ethyl ester (1.4 g, 9.7 mmol) for 72 hours. Purify the crude material by flash chromatography (silica gel) using 5% (7 M ammoniated methanol) in dichloromethane to afford the title compound (0.78 g). $^1$H NMR (CDCl$_3$) δ 0.81 (t, 3H), 1.13 (s, 6H), 1.53 (q, 2H), 3.88 (s, 2H), 7.05 (bs, 1H).

The following compound was prepared essentially by the method of Preparation 13.

| Prep. No. | Chemical name | Structure | Physical data |
|---|---|---|---|
| 14 | 2,3-dimethyl-butanehydrazide | ![structure] | $^1$H NMR (CDCl$_3$) δ 0.86-0.95 (m, 6H), 1.11 (d, 3H), 1.79-1.89 (m, 2H), 3.89 (s, 2H), 6.67 (bs, 1H). |

EXAMPLE 1

Synthesis of 3-tert-butyl-7-[3-(4-fluorophenyl)-1,2,4-oxadiazol-5-yl]-5,6,7,8-tetrahydro[1,2,4]triazolo[4,3-a]pyridine

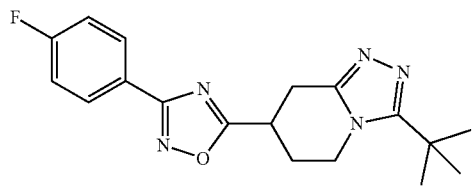 [SMILES: CC(C)(C)c1nnc2n1CCC(c1nc(-c3ccc(F)cc3)no1)C2]

Add 4-fluorobenzamidoxime (4.61 g, 29.93 mmol) to a 1M solution of potassium t-butoxide (27.6 mL, 27.63 mmol) in tetrahydrofuran. Add methyl 3-tert-butyl-5,6,7,8-tetrahydro[1,2,4]triazolo[4,3-a]pyridine-7-carboxylate (6.07 g, 23.02 mmol) and stir overnight at room temperature. Dissolve the reaction in a 1:1 mixture of 50% saturated aqueous sodium bicarbonate and ethyl acetate. Separate layers and extract the aqueous layer with additional ethyl acetate. Wash the combined organic layers with brine, dry over anhydrous sodium sulfate, filter, and concentrate under reduced pressure. Purify the resulting residue by flash chromatography (silica gel), eluting with first 25-100% ethyl acetate:hexane and then 5% methanol in ethyl acetate. Recrystallize from dichloromethane and hexane to afford the title compound as a white solid (3.96 g). Mass spectrum (m/z): 342 (M+1).

Alternative Preparation of 3-tert-butyl-7-[3-(4-fluorophenyl)-1,2,4-oxadiazol-5-yl]-5,6,7,8-tetrahydro[1,2,4]triazolo[4,3-a]pyridine Add dropwise potassium tert-butoxide 1M in tetrahydrofuran (2.08 Kg, 2.08 mol) to a solution of ethyl 3-tert-butyl-5,6,7,8-tetrahydro[1,2,4]triazolo[4,3-a]pyridine-7-carboxylate (455 g, 1.81 mol) and 4-fluorobenzamidoxime (320 g, 2.08 mol) in tetrahydrofuran (11 L) at room temperature. Stir the reaction mixture for 16 hours. Pour the mixture over a solution of saturated sodium bicarbonate (6 L) and add brine (3×2 L). Separate phases and extract aqueous phase with ethyl acetate (3×1 L). Combine organics, dry over magnesium sulfate, filter, and concentrate to dryness under reduced pressure. Purify the resulting residue by silica gel chromatography eluting with ethyl acetate to ethyl acetate:methanol (9:1) to provide the title compound as a white solid (330 g). Mass spectrum (m/z): 342 (M+1).

EXAMPLE 2

Synthesis of 5-(3-tert-butyl-5,6,7,8-tetrahydro[1,2,4]triazolo[4,3-a]pyridin-7-yl)-3-(p-tolyl)-1,2,4-oxadiazole

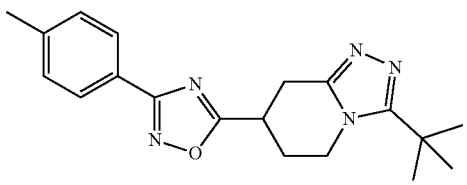 [SMILES: Cc1ccc(-c2noc(C3CCn4c(nnc4C(C)(C)C)C3)n2)cc1]

Add 4-methylbenzamidoxime (1.44 g, 9.3 mmol) to a 1M solution of potassium tert-butoxide (8.6 mL, 8.6 mmol) diluted with tetrahydrofuran (120 mL). Add ethyl 3-t-butyl-5,6,7,8-tetrahydro[1,2,4]triazolo[4,3-a]pyridine-7-carboxylate (2.0 g, 7.2 mmol) and stir overnight at room temperature. Dissolve the reaction in a 1:1 mixture of half saturated aqueous sodium bicarbonate and ethyl acetate. Separate the phases and extract the aqueous phase with ethyl acetate. Wash the combined organic layers with aqueous saturated sodium chloride, dry over anhydrous sodium sulfate, filter, and concentrate under reduced pressure. Purify the resulting residue by silica gel flash chromatography eluting with 25-100% ethyl acetate:hexane followed by 5% methanol:ethyl acetate. Recrystallize from dichloromethane and hexane to afford the title compound as a white solid (1.19 g). $^1$H NMR (CDCl$_3$) δ 1.46 (s, 9H), 2.4 (s, 4H), 2.59 (m, 1H), 3.4 (m, 1H), 3.54-3.69 (m, 2H), 4.11 (m, 1H), 4.38 (m, 1H), 7.22-7.33 (m, 2H), 7.9-7.98 (m, 2H).

The following compounds are prepared essentially by the method of Example 2.

| Example No. | Chemical name | Structure | Physical data |
|---|---|---|---|
| 3 | 5-(3-tert-butyl-5,6,7,8-tetrahydro-[1,2,4]triazolo[4,3-a]pyridin-7-yl)-3-(4-chlorophenyl)-1,2,4-oxadiazole | 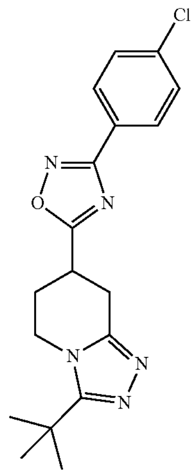 [SMILES: CC(C)(C)c1nnc2n1CCC(c1nc(-c3ccc(Cl)cc3)no1)C2] | MS (m/z): 358/360(M + 1). |
| 4 | 5-[3-(1,1-dimethylpropyl)-5,6,7,8-tetrahydro-[1,2,4]triazolo[4,3-a]pyridin-7-yl]-3-(4-fluorophenyl)-1,2,4-oxadiazole | 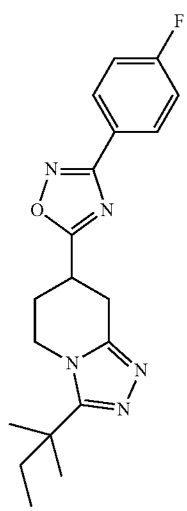 [SMILES: CCC(C)(C)c1nnc2n1CCC(c1nc(-c3ccc(F)cc3)no1)C2] | MS (m/z): 356(M + 1). |
| 5 | 5-[3-(2,2-dimethylpropyl)-5,6,7,8-tetrahydro-[1,2,4]triazolo[4,3-a]pyridin-7-yl]-3-phenyl-1,2,4-oxadiazole | 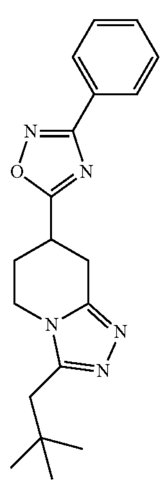 [SMILES: CC(C)(C)Cc1nnc2n1CCC(c1nc(-c3ccccc3)no1)C2] | MS (m/z): 338(M + 1). |
| 6 | 5-(3-isobutyl-5,6,7,8-tetrahydro-[1,2,4]triazolo[4,3-a]pyridin-7-yl)-3-phenyl-1,2,4-oxadiazole | 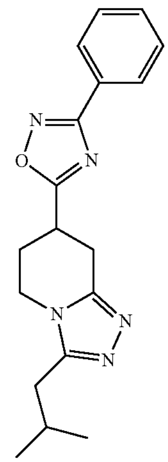 [SMILES: CC(C)Cc1nnc2n1CCC(c1nc(-c3ccccc3)no1)C2] | MS (m/z): 324(M + 1). |
| 7 | 5-[3-(2,2-dimethylpropyl)-5,6,7,8-tetrahydro-[1,2,4]triazolo[4,3-a]pyridin-7-yl]-3-(4-fluorophenyl)-1,2,4-oxadiazole | 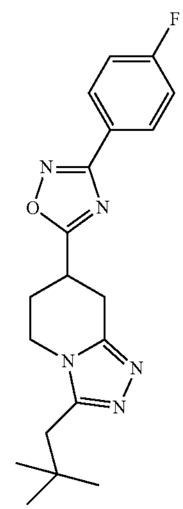 [SMILES: CC(C)(C)Cc1nnc2n1CCC(c1nc(-c3ccc(F)cc3)no1)C2] | MS (m/z): 356(M + 1). |

EXAMPLE 8

Synthesis of 5-[3-(1,1-dimethylpropyl)-5,6,7,8-tetrahydro[1,2,4]triazolo[4,3-a]pyridin-7-yl]-3-phenyl-1,2,4-oxadiazole

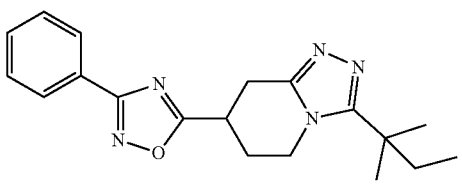 [SMILES: CCC(C)(C)c1nnc2n1CCC(c1nc(-c3ccccc3)no1)C2]

Reflux 2,2-dimethyl-butyric acid hydrazide (0.053 g, 0.48 mmol) and 5-(2-methoxy-3,4,5,6-tetrahydropyridin-4-yl)-3-phenyl-1,2,4-oxadiazole (0.1 g, 0.39 mmol) in methanol (1.55 mL) overnight. Remove the methanol under reduced pressure and replace with acetic acid (2 mL). Reflux the reaction for 3 hours and pour over aqueous saturated sodium bicarbonate. Extract with dichloromethane and dry the organics over anhydrous sodium sulfate, filter, and concentrate under reduced pressure. Purify the resulting residue by flash chromatography eluting with 5-15% ethyl acetate in dichloromethane. Recrystallize from ethyl acetate and hexane to afford the title compound as a crystalline solid (0.078 g). Mass spectrum (m/z): 338 (M+1).

The following compounds are prepared essentially by the method of Example 8.

Alternative Chromatographic Separation of (±)-3-tert-butyl-7-[3-(4-fluorophenyl)-1,2,4-oxadiazol-5-yl]-5,6,7,8-tetrahydro[1,2,4]triazolo[4,3-a]pyridine Purify 321 g of (±)-5-(3-tert-butyl-5,6,7,8-tetrahydro-[1,2,4]triazolo[4,3-a]pyridin-7-yl)-3-(4-fluorophenyl)-1,2,4-oxa-

| Example No. | Chemical name | Structure | Physical data |
| --- | --- | --- | --- |
| 9 | 5-[3-(1,2-dimethylpropyl)-5,6,7,8-tetrahydro-[1,2,4]triazolo[4,3-a]pyridin-7-yl]-3-phenyl-1,2,4-oxadiazole | 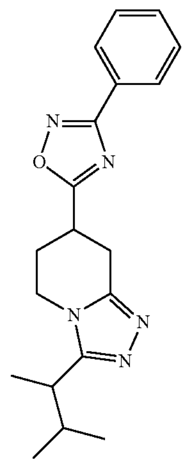 [SMILES: CC(C)C(C)c1nnc2n1CCC(c1nc(-c3ccccc3)no1)C2] | MS (m/z): 338(M + 1). |
| 10 | 5-(3-tert-butyl-5,6,7,8-tetrahydro-[1,2,4]triazolo[4,3-a]pyridin-7-yl)-3-phenyl-1,2,4-oxadiazole | 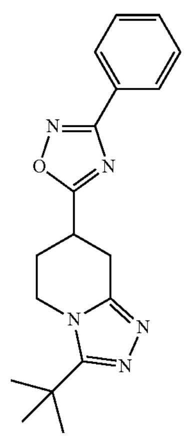 [SMILES: CC(C)(C)c1nnc2n1CCC(c1nc(-c3ccccc3)no1)C2] | MS (m/z): 324(M + 1). |

General Method 1

General Procedure for the Chromatographic Separation of a Racemic Mixture into Individual Enantiomers The appropriate racemic compound, such as (±)-3-tert-butyl-7-[3-(4-fluorophenyl)-1,2,4-oxadiazol-5-yl]-5,6,7,8-tetrahydro[1,2,4]triazolo[4,3-a]pyridine (1.0 g, 2.9 mmol) is dissolved in a solution of methanol. The solution is separated via supercritical fluid chromatography utilizing 21.2×250 mm Daicel Chiralpak(R) AD-H, 5 um eluting isocratically with 30% methanol:carbon dioxide at a flow rate of 70 mL/min, collecting at a wavelength of 225 nm, to afford 434 mg of the first eluting fraction, designated isomer 1 and 448 mg of the second eluting fraction, designated isomer 2 (Example 11, 95% ee).

diazole (330 g) by chiral HPLC, detection at 265 nm, in 11×33 cm Chiralpak AD column, using ethanol/acetonitrile 95/5 as eluent, flow rate 750 ml/min, SSR (Steady state recycle method) to provide 150 g of the desired compound, isomer 2, as a white solid. mass spectrum (m/z): 342 (M+1), 97.8 ee, $[\alpha]_D^{20}$=–11° (C=1.0, EtOH).

The following compounds are prepared essentially as described in General Method 1. The retention times shown under physical data are determined via analytical supercritical fluid chromatography utilizing a 4.6 mm×150 mm Daicel Chiralpak AD-H eluting isocratically with 30% methanol: carbon dioxide at a flow rate of 5 mL/min, viewing at a wavelength of 230 nm.

| Example No. | Chemical Name | Structure | Physical Data | k' |
|---|---|---|---|---|
| 11 | (−)-3-tert-butyl-(7S)-[3-(4-fluorophenyl)-1,2,4-oxadiazol-5-yl]-5,6,7,8-tetrahydro[1,2,4]triazolo[4,3-a]pyridine (isomer 2) | 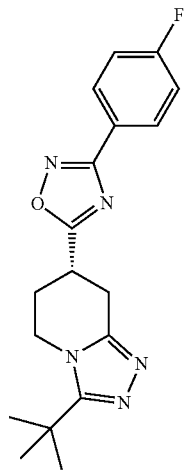 [SMILES: CC(C)(C)c1nnc2n1CC[C@H](c1nc(-c3ccc(F)cc3)no1)C2] | 95% e.e. Retention time: 1.32 min. (97.6%); $[\alpha]_D^{20} = -10.6°$ (c = 1.0, EtOH) | 3.4 |
| 12 | (−)-5-(3-tert-butyl-5,6,7,8-tetrahydro-[1,2,4]triazolo[4,3-a]pyridin-7-yl)-3-phenyl-1,2,4-oxadiazole (isomer 2) | 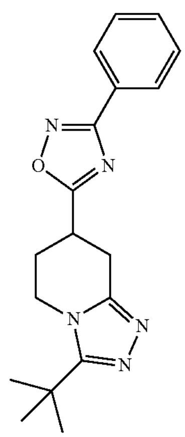 [SMILES: CC(C)(C)c1nnc2n1CCC(c1nc(-c3ccccc3)no1)C2] | 96% e.e. Retention time: 1.69 min. (98%) $[\alpha]_D^{20} = -11.6°$ (c = 1.0, EtOH) | 4.6 |
| 13 | (−)-5-(3-tert-butyl-5,6,7,8-tetrahydro-[1,2,4]triazolo[4,3-a]pyridin-7-yl)-3-(4-chlorophenyl)-1,2,4-oxadiazole (isomer 2) | 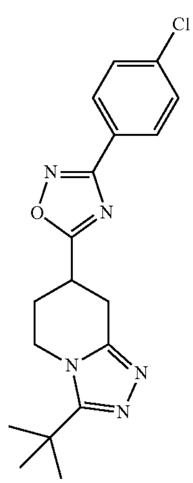 [SMILES: CC(C)(C)c1nnc2n1CCC(c1nc(-c3ccc(Cl)cc3)no1)C2] | >99% e.e. Retention time: 2.28 min. (100%) $[\alpha]_D^{20} = -10.3°$ (c = 1.0, EtOH) | 6.6 |

Procedure for the Chromatographic Separation of (±)-5-[3-(1,1-dimethylpropyl)-5,6,7,8-tetrahydro[1,2,4]triazolo[4,3-a]pyridin-7-yl]-3-(4-fluorophenyl)-1,2,4-oxadiazole Compound (±) 5-[3-(1,1-dimethylpropyl)-5,6,7,8-tetrahydro-[1,2,4]triazolo[4,3-a]pyridin-7-yl]-3-(4-fluorophenyl)-1,2,4-oxadiazole(0.60 g, 1.69 mmol) is dissolved in methanol. The solution is separated via supercritical fluid chromatography utilizing 21.2×250 mm Daicel Chiralpak AS-H, 5 um eluting isocratically with 25% ethanol:carbon dioxide at a flow rate of 70 mL/min, collecting at a wavelength of 225 nm, to afford 240 mg of the first eluting fraction, designated isomer 1 (Example 14, >99% e.e.), and 233 mg of the second eluting fraction, designated isomer 2.

The retention time shown under physical data is determined via analytical supercritical fluid chromatography utilizing a 4.6 mm×150 mm Daicel Chiralpak AS-H eluting isocratically with 25% ethanol:carbon dioxide at a flow rate of 5 mL/min, viewing at a wavelength of 230 nm.

| Example No. | Chemical Name | Structure | Physical Data | k' |
|---|---|---|---|---|
| 14 | (−)-5-[3-(1,1-dimethylpropyl)-5,6,7,8-tetrahydro-[1,2,4]triazolo[4,3-a]pyridin-7-yl]-3-(4-fluorophenyl)-1,2,4-oxadiazole (isomer 1) | 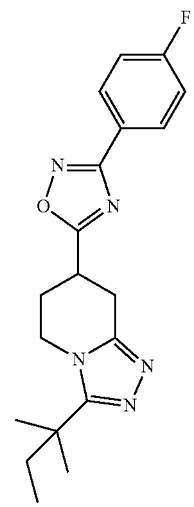 [SMILES: CCC(C)(C)c1nnc2n1CCC(c1nc(-c3ccc(F)cc3)no1)C2] | >99% e.e. Retention time: 1.57 min. (100%) $[\alpha]_D^{20} = -16.4°$ (c = 1.0, EtOH) | 4.2 |

Procedure for the Chromatographic Separation of (±)-5-[3-(1,1-dimethylpropyl)-5,6,7,8-tetrahydro-[1,2,4]triazolo[4,3-a]pyridin-7-yl]-3-phenyl-1,2,4-oxadiazole Compound (±)-5-[3-(1,1-dimethylpropyl)-5,6,7,8-tetrahydro-[1,2,4]triazolo[4,3-a]pyridin-7-yl]-3-phenyl-1,2,4-oxadiazole (2.465 g, 7.3 mmol) is dissolved in ethanol. The solution is separated via polar organic chiral chromatography utilizing 8×38 cm Daicel Chiralpak AD-H eluting isocratically with 100% ethanol at a flow rate of 425 mL/min, collecting at a wavelength of 240 nm, to afford 1.04 g of the first eluting fraction, designated isomer 1, and 0.98 g of the second eluting fraction, designated isomer 2 (Example 15, >99% e.e.).

The retention times shown under physical data are determined via analytical polar organic chiral chromatography utilizing 4.6 mm×150 mm Daicel Chiralpak AD eluting isocratically with 100% methanol with 0.2% dimethylethylamine at a flow rate of 0.6 mL/min, viewing at a wavelength of 250 nm.

| Example No. | Chemical Name | Structure | Physical Data | k' |
|---|---|---|---|---|
| 15 | (−)-5-[3-(1,1-dimethylpropyl)-5,6,7,8-tetrahydro-[1,2,4]triazolo[4,3-a]pyridin-7-yl]-3-phenyl-1,2,4-oxadiazole (isomer 2) | 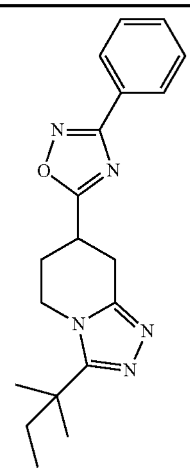 | >99% e.e. Retention time: 8.2 min. (100%) $[\alpha]_D^{20}=-16.9°$ (c = 1.0, EtOH) | 2.28 |

Procedure for the Chromatographic Separation of (±)-5-(3-tert-butyl-5,6,7,8-tetrahydro-[1,2,4]triazolo[4,3-a]pyridin-7-yl)-3-(p-tolyl)-1,2,4-oxadiazole Compound (±)-5-(3-tert-butyl-5,6,7,8-tetrahydro-[1,2,4]triazolo[4,3-a]pyridin-7-yl)-3-(p-tolyl)-1,2,4-oxadiazole (1.19 g, 3.5 mmol) is dissolved in methanol. The solution is separated via polar organic chiral chromatography utilizing a 30×250 mm Daicel Chiralpak AD-H, 5 um eluting isocratically with 100% methanol at a flow rate of 30 mL/min, collecting at a wavelength of 225 nm, to afford 323 mg of the first eluting fraction, designated isomer 1, and 440 mg of the second eluting fraction, designated isomer 2 (Example 16, 97.8% e.e.).

The retention time shown under physical data is determined via analytical polar organic chiral chromatography utilizing 4.6 mm×150 mm Daicel Chiralpak AD-H eluting isocratically with 100% methanol with 0.2% dimethylethylamine at a flow rate of 1 mL/min, collecting at a wavelength of 240 nm

| Example No. | Chemical Name | Structure | Physical Data | k' |
|---|---|---|---|---|
| 16 | (−)-5-(3-tert-butyl-5,6,7,8-tetrahydro-[1,2,4]triazolo[4,3-a]pyridin-7-yl)-3-(p-tolyl)-1,2,4-oxadiazole (isomer 2) | 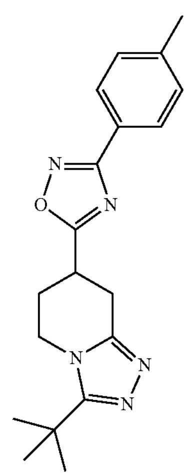 [SMILES: Cc1ccc(-c2noc(C3CCn4c(nnc4C(C)(C)C)C3)n2)cc1] | 97.8% e.e. Retention time: 4.21 min. (99%) $[\alpha]_D^{20}=-10.7°$ (c = 1.0, EtOH) | 1.8 |

We claim:

1. A compound of the formula or a pharmaceutically acceptable salt thereof

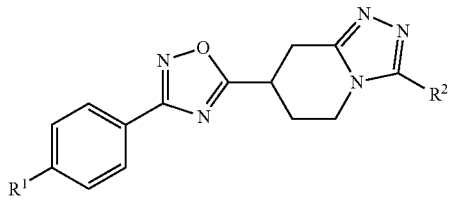

wherein
$R^1$ is hydrogen, fluoro, chloro or methyl; and
$R^2$ is C4-C5 branched alkyl.

2. The compound or salt of claim 1 wherein $R^1$ is fluoro.

3. The compound or salt of claim 1 wherein $R^2$ is tert-butyl.

4. The compound or salt of claim 1 wherein
$R^1$ is hydrogen, fluoro, chloro or methyl; and
$R^2$ is tert-butyl, 1,1-dimethylpropyl, 2,2-dimethylpropyl, isobutyl, or 1,2-dimethylpropyl.

5. The compound or salt as claimed in claim 1 which is (−)-3-tert-butyl-(7S)-[3-(4-fluorophenyl)-1,2,4-oxadiazol-5-yl]-5,6,7,8-tetrahydro[1,2,4]-triazolo[4,3-a]pyridine.

6. A pharmaceutical composition comprising a compound as claimed in claim 1, or a pharmaceutically acceptable salt thereof, and a pharmaceutically acceptable carrier, diluent or excipient.

7. A process for preparing a compound of formula I, or a pharmaceutically acceptable salt thereof, comprising
A) for a compound of formula I,

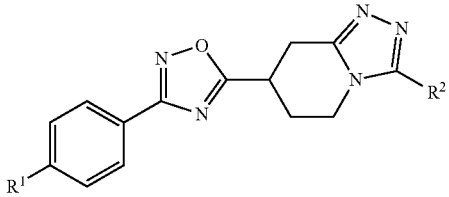

wherein
$R^1$ is hydrogen, fluoro, chloro or methyl; and
$R^2$ is C4-C5 branched alkyl;

condensing of a compound of formula VII with a compound of formula II wherein $R^3$ is C1-C3 alkyl

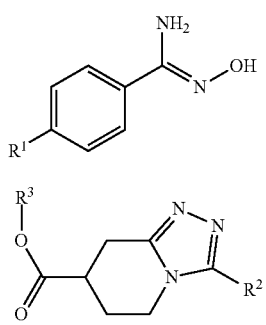

or alternatively
B) for a compound of formula I, condensing an $R^2$-acyl hydrazine with a compound of formula III wherein X is O or S, and $R^4$ is C1-C3 alkyl.

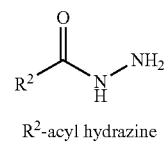

$R^2$-acyl hydrazine

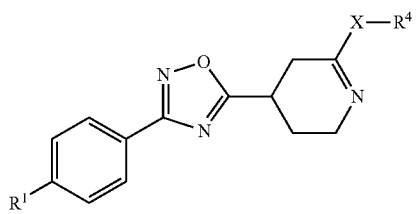

whereafter, when a pharmaceutically acceptable salt of the compound of formula I is desired, it is obtained by reacting a basic compound of formula I with a physiologically acceptable acid.

* * * * *

UNITED STATES PATENT AND TRADEMARK OFFICE
CERTIFICATE OF CORRECTION

PATENT NO. : 8,592,590 B2  
APPLICATION NO. : 13/515407  
DATED : November 26, 2013  
INVENTOR(S) : Lourdes Prieto and Lorena Taboada Martinez Page 1 of 1

It is certified that error appears in the above-identified patent and that said Letters Patent is hereby corrected as shown below:

Title page, Column 2 (Abstract), Line 5, Delete "C4-CS" and insert -- C4-C5 --, therefor.

Signed and Sealed this  
Eighteenth Day of February, 2014

Michelle K. Lee  
*Deputy Director of the United States Patent and Trademark Office*